(12) United States Patent
Yang et al.

(10) Patent No.: US 7,427,661 B2
(45) Date of Patent: Sep. 23, 2008

(54) CANINE IL-5 PROTEINS AND FRAGMENTS THEREOF

(75) Inventors: Shumin Yang, Palo Alto, CA (US); Catherine A. McCall, Boulder, CO (US); Eric R. Weber, Fort Collins, CO (US)

(73) Assignee: Heska Corporation, Loveland, CO (US)

( * ) Notice: Subject to any disclaimer, the term of this patent is extended or adjusted under 35 U.S.C. 154(b) by 0 days.

(21) Appl. No.: 11/561,562

(22) Filed: Nov. 20, 2006

(65) Prior Publication Data

US 2007/0141671 A1 Jun. 21, 2007

Related U.S. Application Data

(60) Division of application No. 10/787,382, filed on Feb. 24, 2004, now Pat. No. 7,183,080, which is a continuation of application No. 09/755,633, filed on Jan. 5, 2001, now abandoned, which is a continuation-in-part of application No. 09/322,409, filed on May 28, 1999, now Pat. No. 6,471,957.

(60) Provisional application No. 60/087,306, filed on May 29, 1998.

(51) Int. Cl.
C07K 14/52 (2006.01)
C12N 15/19 (2006.01)

(52) U.S. Cl. ............... 530/351; 536/23.5; 435/69.5

(58) Field of Classification Search ............... None
See application file for complete search history.

(56) References Cited

U.S. PATENT DOCUMENTS 5,831,023 A 11/1998 Capon et al.

FOREIGN PATENT DOCUMENTS

| EP | 0 186 098 A1 | 7/1986 |
| EP | 0 322 870 A2 | 7/1989 |
| EP | 0 414 355 A1 | 2/1991 |
| EP | 0 759 468 A1 | 2/1997 |
| EP | 0 875 251 A1 | 11/1998 |
| WO | WO 99/61618 | 12/1999 |

OTHER PUBLICATIONS

Mikayama et al. Proc. Natl. Acad. Sci. USA vol. 90, pp. 10056-10060.*
Voet et al. Biochemistry John Wiley & Sons, Inc., pp. 126-128 and 228-234.*
Armitage et al., *Seminars in Immunology*, vol. 5, 1993, pp. 401-412.
Armitage et al., *Nature*, vol. 357, 1992, pp. 80-82.
Azuma et al., *Nucleic Acids Research*, vol. 14, No. 22, 1986, pp. 9149-9158.
Brown et al., *Journal of Immunology*, vol. 142, No. 2, 1989, pp. 679-687.
Cantrell et al., *Proc. Natl., Acad. Sci. USA*, vol. 82, 1985, pp. 6250-6254.
Daugherty et al., *Journal of Interferon Research*, vol. 4, 1984, pp. 635-643.
Dion et al., *Biochemical and Biophysical Research Communications*, vol. 138, No. 2, 1986, pp. 826-834.
Drexler, *Leukemia*, vol. 10, 1996, pp. 588-599.
Feng et al., *J. Mol. Evol.*, vol. 21, 1985, pp. 112-125.
Gauchat et al., *Res. Immunol.*, vol. 145(3), Mar.-Apr. 1994, pp. 240-249.
Gauchat et al., *FEBS 11964*, vol. 315, No. 3, 1993, pp. 259-266.
Goeddel et al., *Nature*, vol. 290, 1981, pp. 20-26.
Gough et al., *The EMBO Journal*, vol. 4, No. 3, 1985, pp. 645-653.
Graf et al., *Eur. J. Immunol.*, vol. 22, 1992, pp. 3191-3194.
Grimaldi et al., *Journal of Immunology*, vol. 149, No. 12, 1992, pp. 3921-3926.
Hannum et al., *Nature*, vol. 368, 1994, pp. 643-648.
Heussler et al., *Gene*, vol. 114, 1992, pp. 273-278.
Himmler et al., *Journal of Interferon Research*, vol. 7, 1987, pp. 173-183.
Hirano et al., *Immunology*, vol. 90, 1997, pp. 294-300.
Hollenbaugh et al., *The EMBO Journal*, vol. 11, No. 12, 1992, pp. 4313-4321.
Inumaru et al., *Immunology and Cell Biology*, vol. 73, 1995, pp. 474-476.
Johnson et al., *J. Mol. Biol.*, vol. 233, 1993, pp. 716-738.
Kelley et al., *Nucleic Acids Research*, vol. 13, No. 3, 1985, pp. 805-823.
Lakkis et al., *Biochemical and Biophysical Research Communications*, vol. 197, No. 2, 1993, pp. 612-618.
Leong et al., *Veterinary Immunology and Immunopathology*, vol. 21, 1989, pp. 261-278.
Lerner et al., GenBank Accession No. U39634, submitted Oct. 27, 1995.
Lerner et al., GenBank Accession No. AAB42052 (U39534.1), submitted Oct. 27, 1995.
Lyman et al., *Blood*, vol. 83, No. 10, 1994, pp. 2795-2801.
Lyman et al., *Oncogene*, vol. 10, 1995, pp. 149-157.
Lyman et al., *Cell*, vol. 75, 1993, pp. 1157-1167.
Lyman et al., *Oncogene*, vol. 11, 1995, pp. 1165-1172.

(Continued)

*Primary Examiner*—Prema Mertz

(57) ABSTRACT

The present invention relates to canine interleukin-5 proteins; canine interleukin-5 nucleic acid molecules, including those that encode canine interleukin-5 proteins; to antibodies raised against such proteins; and to inhibitory compounds that regulate such proteins. The present invention also includes methods to identify and obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to regulate an immune response in an animal.

3 Claims, No Drawings

OTHER PUBLICATIONS

McClanahan et al., *Blood*, vol. 88, No. 9, 1996, pp. 3371-3382.
McInnes et al., *Gene*, vol. 105, 1991, pp. 275-279.
McKenzie et al., *Proc. Natl. Acad. Sci. USA*, vol. 90, 1993, pp. 3735-3739.
Mertens et al., *Immunogenetics*, vol. 42, 1995, pp. 430-431.
Minty et al., *Nature*, vol. 362, 1993, pp. 248-250.
Nagata et al., *Nature*, vol. 287, 1980, pp. 401-408.
Nakamura et al., *Biosci. Biotech. Biochem.*, vol. 56, No. 2, 1992, pp. 211-214.
Nash et al., *Blood*, vol. 78, No. 4, 1991, pp. 930-937.
Navarro et al., *J. Gen. Virol.* vol. 70, 1989, pp. 1381-1389.
O'Brien et al., *Immunology and Cell Biology*, vol. 69, 1991, pp. 51-55.
Osorio et al., *Vaccine*, vol. 17, 1999, pp. 1109-1116.
Padrid et al., *AJVR*, vol. 59, No. 10, 1998, pp. 1263-1269.
Patterson et al., *Journal of Clinical Investigation*, vol. 44, No. 1, 1965, pp. 140-148.
Seow et al., *Gene*, vol. 124, 1993, pp. 291-293.
Sideras et al., *Adv. Exp. Med. Biol.*, vol. 213, 1987, pp. 227-236.
Stamenkovic et al., *The EMBO Journal*, vol. 8, No. 5, 1989, pp. 1403-1410.
Torres et al., *Journal of Immunology*, vol. 148, No. 2, 1992, pp. 620-626.
Wong et al., *Science*, vol. 228, 1985, pp. 810-815.
Yokota et al., *Proc. Natl. Acad. Sci. USA*, vol. 83, 1986, pp. 5894-5898.
Zhou et al., GenBank Accession No. L12991.
Van Der Kaaij, et al., 1999, "Immunogenetics," vol. 49, pp. 142-143.
Ueda, et al., 1993, *Journal of Verterinary Medical Science*, vol. 55, No. 2, pp. 251-258, XP001001462.
Watts, et al., 1999, *Int. J. Parasitology*, 29:1149-1163.
Yang, et al., 2001, *J Interferon Cytokine Res*, 21(6):361-7.

* cited by examiner

```
                              SEQUENCE LISTING

<160> NUMBER OF SEQ ID NOS: 21

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
atgcactttc tttgcc                                                          16

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
ctggaggaaa akacttcrat gattctgata tctgaaatat at                             42

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
ctgacycttk sttggscctc attctca                                              27

<210> SEQ ID NO 4
<211> LENGTH: 610
<212> TYPE: DNA
<213> ORGANISM: Canis familiaris
<220> FEATURE:
<221> NAME/KEY: CDS
<222> LOCATION: (29)..(430)

<400> SEQUENCE: 4
caaggcaaac actgaacatt tcagagct atg aga atg ctt ctg aat ttg agt             52
                            Met Arg Met Leu Leu Asn Leu Ser
                              1               5 ttg cta gct ctt ggg gct gcc tat gtt tct gcc ttt gct gta gaa aat           100
Leu Leu Ala Leu Gly Ala Ala Tyr Val Ser Ala Phe Ala Val Glu Asn
         10                  15                  20 ccc atg aat aga ctg gtg gca gag acc ttg aca ctg ctc tcc act cat           148
Pro Met Asn Arg Leu Val Ala Glu Thr Leu Thr Leu Leu Ser Thr His
 25                  30                  35                  40 cga act tgg ctg ata ggc gat ggg aac ctg atg att cct act cct gaa           196
Arg Thr Trp Leu Ile Gly Asp Gly Asn Leu Met Ile Pro Thr Pro Glu
                 45                  50                  55 aat aaa aat cac caa ctg tgc att aaa gaa gtt ttt cag ggt ata gac           244
Asn Lys Asn His Gln Leu Cys Ile Lys Glu Val Phe Gln Gly Ile Asp
```

```
                60                  65                  70
aca ttg aag aac caa act gcc cac ggg gag gct gtg gat aaa cta ttc    292
Thr Leu Lys Asn Gln Thr Ala His Gly Glu Ala Val Asp Lys Leu Phe
         75                  80                  85 caa aac ttg tct tta ata aaa gaa cac ata gag cgc caa aaa aaa agg    340
Gln Asn Leu Ser Leu Ile Lys Glu His Ile Glu Arg Gln Lys Lys Arg
 90                  95                 100 tgt gca gga gaa aga tgg aga gtg aca aag ttc cta gac tac ctg caa    388
Cys Ala Gly Glu Arg Trp Arg Val Thr Lys Phe Leu Asp Tyr Leu Gln
105                 110                 115                 120 gta ttt ctt ggt gta ata aac acc gag tgg aca ccg gaa agt            430
Val Phe Leu Gly Val Ile Asn Thr Glu Trp Thr Pro Glu Ser
                125                 130 tgagaacaaa ccggcttatt gtagtggaag attttggaga agaatggttt tttggcgatg   490
agaatgaggg ccaaccaaca gtagggactt aatggccagt ataactaagc ttcagagaca   550
aagtaaatat ttcaggcatc ctactacttt atcacttcac acagatgaaa tatatttgag   610

<210> SEQ ID NO 5
<211> LENGTH: 134
<212> TYPE: PRT
<213> ORGANISM: Canis familiaris

<400> SEQUENCE: 5

Met Arg Met Leu Leu Asn Leu Ser Leu Leu Ala Leu Gly Ala Ala Tyr
  1               5                  10                  15

Val Ser Ala Phe Ala Val Glu Asn Pro Met Asn Arg Leu Val Ala Glu
                 20                  25                  30

Thr Leu Thr Leu Leu Ser Thr His Arg Thr Trp Leu Ile Gly Asp Gly
             35                  40                  45

Asn Leu Met Ile Pro Thr Pro Glu Asn Lys Asn His Gln Leu Cys Ile
         50                  55                  60

Lys Glu Val Phe Gln Gly Ile Asp Thr Leu Lys Asn Gln Thr Ala His
 65                  70                  75                  80

Gly Glu Ala Val Asp Lys Leu Phe Gln Asn Leu Ser Leu Ile Lys Glu
                 85                  90                  95

His Ile Glu Arg Gln Lys Lys Arg Cys Ala Gly Glu Arg Trp Arg Val
            100                 105                 110

Thr Lys Phe Leu Asp Tyr Leu Gln Val Phe Leu Gly Val Ile Asn Thr
        115                 120                 125

Glu Trp Thr Pro Glu Ser
    130

<210> SEQ ID NO 6
<211> LENGTH: 610
<212> TYPE: DNA
<213> ORGANISM: Canis familiaris

<400> SEQUENCE: 6
ctcaaatata tttcatctgt gtgaagtgat aaagtagtag gatgcctgaa atatttactt    60
tgtctctgaa gcttagttat actggccatt aagtccctac tgttggttgg ccctcattct   120
catcgccaaa aaaccattct tctccaaaat cttccactac aataagccgg tttgttctca   180
actttccggt gtccactcgg tgtttattac accaagaaat acttgcaggt agtctaggaa   240
ctttgtcact ctccatcttt ctcctgcaca cctttttttt tggcgctcta tgtgttcttt   300
tattaaagac aagttttgga atagtttatc cacagcctcc ccgtgggcag tttggttctt   360
```

```
caatgtgtct ataccctgaa aaacttcttt aatgcacagt tggtgatttt tattttcagg    420
agtaggaatc atcaggttcc catcgcctat cagccaagtt cgatgagtgg agagcagtgt    480
caaggtctct gccaccagtc tattcatggg attttctaca gcaaaggcag aaacataggc    540
agccccaaga gctagcaaac tcaaattcag aagcattctc atagctctga aatgttcagt    600
gtttgccttg                                                            610
```

<210> SEQ ID NO 7
<211> LENGTH: 402
<212> TYPE: DNA
<213> ORGANISM: Canis familiaris

<400> SEQUENCE: 7

```
atgagaatgc ttctgaattt gagtttgcta gctcttgggg ctgcctatgt ttctgccttt     60
gctgtagaaa atcccatgaa tagactggtg gcagagacct tgacactgct ctccactcat    120
cgaacttggc tgataggcga tgggaacctg atgattccta ctcctgaaaa taaaaatcac    180
caactgtgca ttaaagaagt ttttcagggt atagacacat tgaagaacca aactgcccac    240
ggggaggctg tggataaact attccaaaac ttgtctttaa taaaagaaca catagagcgc    300
caaaaaaaaa ggtgtgcagg agaaagatgg agagtgacaa agttcctaga ctacctgcaa    360
gtatttcttg gtgtaataaa caccgagtgg acaccggaaa gt                       402
```

<210> SEQ ID NO 8
<211> LENGTH: 402
<212> TYPE: DNA
<213> ORGANISM: Canis familiaris

<400> SEQUENCE: 8

```
actttccggt gtccactcgg tgtttattac accaagaaat acttgcaggt agtctaggaa     60
ctttgtcact ctccatcttt ctcctgcaca ccttttttt tggcgctcta tgtgttcttt    120
tattaaagac aagttttgga atagtttatc cacagcctcc ccgtgggcag tttggttctt    180
caatgtgtct ataccctgaa aaacttcttt aatgcacagt tggtgatttt tattttcagg    240
agtaggaatc atcaggttcc catcgcctat cagccaagtt cgatgagtgg agagcagtgt    300
caaggtctct gccaccagtc tattcatggg attttctaca gcaaaggcag aaacataggc    360
agccccaaga gctagcaaac tcaaattcag aagcattctc at                       402
```

<210> SEQ ID NO 9
<211> LENGTH: 345
<212> TYPE: DNA
<213> ORGANISM: Canis familiaris
<220> FEATURE:
<221> NAME/KEY: CDS
<222> LOCATION: (1)..(345)

<400> SEQUENCE: 9

```
ttt gct gta gaa aat ccc atg aat aga ctg gtg gca gag acc ttg aca      48
Phe Ala Val Glu Asn Pro Met Asn Arg Leu Val Ala Glu Thr Leu Thr
 1               5                  10                  15 ctg ctc tcc act cat cga act tgg ctg ata ggc gat ggg aac ctg atg      96
Leu Leu Ser Thr His Arg Thr Trp Leu Ile Gly Asp Gly Asn Leu Met
             20                  25                  30 att cct act cct gaa aat aaa aat cac caa ctg tgc att aaa gaa gtt     144
Ile Pro Thr Pro Glu Asn Lys Asn His Gln Leu Cys Ile Lys Glu Val
         35                  40                  45 ttt cag ggt ata gac aca ttg aag aac caa act gcc cac ggg gag gct     192
Phe Gln Gly Ile Asp Thr Leu Lys Asn Gln Thr Ala His Gly Glu Ala
     50                  55                  60
```

```
              50                  55                   60
gtg gat aaa cta ttc caa aac ttg tct tta ata aaa gaa cac ata gag    240
Val Asp Lys Leu Phe Gln Asn Leu Ser Leu Ile Lys Glu His Ile Glu
 65                  70                  75                  80 cgc caa aaa aaa agg tgt gca gga gaa aga tgg aga gtg aca aag ttc    288
Arg Gln Lys Lys Arg Cys Ala Gly Glu Arg Trp Arg Val Thr Lys Phe
                 85                  90                  95 cta gac tac ctg caa gta ttt ctt ggt gta ata aac acc gag tgg aca    336
Leu Asp Tyr Leu Gln Val Phe Leu Gly Val Ile Asn Thr Glu Trp Thr
                100                 105                 110 ccg gaa agt                                                        345
Pro Glu Ser
        115

<210> SEQ ID NO 10
<211> LENGTH: 115
<212> TYPE: PRT
<213> ORGANISM: Canis familiaris

<400> SEQUENCE: 10

Phe Ala Val Glu Asn Pro Met Asn Arg Leu Val Ala Glu Thr Leu Thr
  1               5                  10                  15

Leu Leu Ser Thr His Arg Thr Trp Leu Ile Gly Asp Gly Asn Leu Met
                 20                  25                  30

Ile Pro Thr Pro Glu Asn Lys Asn His Gln Leu Cys Ile Lys Glu Val
                 35                  40                  45

Phe Gln Gly Ile Asp Thr Leu Lys Asn Gln Thr Ala His Gly Glu Ala
         50                  55                  60

Val Asp Lys Leu Phe Gln Asn Leu Ser Leu Ile Lys Glu His Ile Glu
 65                  70                  75                  80

Arg Gln Lys Lys Arg Cys Ala Gly Glu Arg Trp Arg Val Thr Lys Phe
                 85                  90                  95

Leu Asp Tyr Leu Gln Val Phe Leu Gly Val Ile Asn Thr Glu Trp Thr
                100                 105                 110

Pro Glu Ser
        115

<210> SEQ ID NO 11
<211> LENGTH: 345
<212> TYPE: DNA
<213> ORGANISM: Canis familiaris

<400> SEQUENCE: 11
actttccggt gtccactcgg tgtttattac accaagaaat acttgcaggt agtctaggaa      60
ctttgtcact ctccatcttt ctcctgcaca cctttttttt tggcgctcta tgtgttcttt     120
tattaaagac aagttttgga atagtttatc cacagcctcc ccgtgggcag tttggttctt     180
caatgtgtct ataccctgaa aaacttcttt aatgcacagt tggtgatttt tattttcagg     240
agtaggaatc atcaggttcc catcgcctat cagccaagtt cgatgagtgg agagcagtgt     300
caaggtctct gccaccagtc tattcatggg attttctaca gcaaa                     345

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 12
gggctcgaga aaagatttgc tgtagaaaat cccatg                              36

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
cccgcggccg ctcaactttc cggtgtccac tc                                  32

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
aggcaaacac tgaacatttc                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
tctccaaaat cttccactac                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
tcaagggagg ctataaattc                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ttatagtcaa gggcatatcc                                                20

<210> SEQ ID NO 18
<211> LENGTH: 1658
<212> TYPE: DNA
<213> ORGANISM: Canis familiaris
<220> FEATURE:
<221> NAME/KEY: intron
<222> LOCATION: (171)..(373)
<220> FEATURE:
<221> NAME/KEY: intron
```

<222> LOCATION: (407)..(1275)
<220> FEATURE:
<221> NAME/KEY: intron
<222> LOCATION: (1405)..(1522)

<400> SEQUENCE: 18

| | | | | | |
|---|---|---|---|---|---|
| aggcaaacac | tgaacatttc | agagctatga | gaatgcttct | gaatttgagt | ttgctagctc | 60 |
| ttggggctgc | ctatgttct | gcctttgctg | tagaaaatcc | catgaataga | ctggtggcag | 120 |
| agaccttgac | actgctctcc | actcatcgaa | cttggctgat | aggcgatggg | gtaattttct | 180 |
| ttttgattcc | tacagtcttt | aaaatgcatg | ggtaattggt | ggtggtggct | agttttaaa | 240 |
| gatccattat | caataatgaa | gtaatgagtg | ttaataatat | ataatgggta | accatgttac | 300 |
| tcagaagaat | tatattaaaa | gttatgaacc | ttacaataca | ttaaaaatga | atgttgtttc | 360 |
| cttttctttt | cagaacctga | tgattcctac | tcctgaaaat | aaaaatgtaa | gttaaattat | 420 |
| gatttgataa | aatgattaca | tgaatcagtt | tcatatttta | agctataaag | tatcagttaa | 480 |
| cattgggatg | atttaatttt | atctattttg | tttttatgtg | tgcggatgta | aattatgtgc | 540 |
| ttatgaatat | taggaatggt | gttaggaatg | gctctacaat | attaagtaga | atccattaag | 600 |
| caagtggatc | aggccctttt | ttgatgttgt | cagttctcca | tctcaaagag | cctcgtgtca | 660 |
| ggcattcttt | ccaaaagaat | tccatattgg | gtcagagata | cttcctaggc | tccattcacc | 720 |
| tctgtcgttg | gctttcctca | cctcaacgtt | tttctgaaag | tactagcaac | ttggggttat | 780 |
| atttttagaa | ttatggtcag | tagacatgaa | aatatacagt | gaagtcctat | attaatagtc | 840 |
| acttccacat | atttaaatga | tttttaactc | taatggaatc | atatacatct | ggagtatgtc | 900 |
| atggtcatat | taaatgttaa | aaatgtgat | atcattagtc | taaatagaat | aaaattacca | 960 |
| gctagaacta | tacgaggaaa | ttctgaggtg | aggtaaatca | gtaaggcagt | tgtattatac | 1020 |
| ctcgtaagca | tttattttc | attaatcatt | tcatttatat | catttgtaac | acttctcagt | 1080 |
| aattatataa | acatcattta | cttatggtaa | ttatagctta | gtataaggtg | gtttcccacc | 1140 |
| tggaaaagac | acaagtaaaa | acctcttggg | agaagggaac | ttgtgtaaac | cccacaaaac | 1200 |
| aaagtctaac | ttttggacc | aaattttat | gccttgtttt | gatgaattat | atttttaaa | 1260 |
| atcttcctca | tttagcacca | actgtgcatt | aaagaagttt | tcagggtat | agacacattg | 1320 |
| aagaaccaaa | ctgcccacgg | ggaggctgtg | gataaactac | tccaaaactt | gtctttaata | 1380 |
| aaagaacaca | tagagcgcca | aaagtaagt | taaagacatt | tggcaaaaac | ttaagtatat | 1440 |
| ttgtctgact | ctgcctgttt | ttttttttt | tttttacaag | aattgacagt | ttcctacaat | 1500 |
| atctcctctg | ttcttttaac | agaaaaggtg | tgcaggagaa | agatggagag | tgacaaagtt | 1560 |
| cctagactac | ctgcaagtat | ttcttggtgt | aataaacacc | gagtggacac | cggaaagttg | 1620 |
| agaacaaacc | ggcttattgt | agtggaagat | tttggaga | | | 1658 |

<210> SEQ ID NO 19
<211> LENGTH: 1658
<212> TYPE: DNA
<213> ORGANISM: Canis familiaris

<400> SEQUENCE: 19

| | | | | | |
|---|---|---|---|---|---|
| tctccaaaat | cttccactac | aataagccgg | tttgttctca | actttccggt | gtccactcgg | 60 |
| tgtttattac | accaagaaat | acttgcaggt | agtctaggaa | ctttgtcact | ctccatcttt | 120 |
| ctcctgcaca | ccttttctgt | taaagaaaca | gaggagatat | tgtaggaaac | tgtcaattct | 180 |
| tgtaaaaaaa | aaaaaaaaaa | acaggcagag | tcagacaaat | atacttaagt | ttttgccaaa | 240 |

```
tgtctttaac ttacttttg gcgctctatg tgttctttta ttaaagacaa gttttggaat      300
agtttatcca cagcctcccc gtgggcagtt tggttcttca atgtgtctat accctgaaaa      360
acttctttaa tgcacagttg gtgctaaatg aggaagattt taaaaaatat aattcatcaa      420
aacaaggcat aaaaatttgg tccaaaagtt agactttgtt ttgtgggtt tacacaagtt      480
cccttctccc aagaggtttt tacttgtgtc ttttccgggt gggaaaccac cttatactaa      540
gctataatta ccataagtaa atgatgttta tataattact gagaagtgtt acaaatgata      600
taaatgaaat gattaatgaa aaataaatgc ttacgaggta taatcaaact gccttactga      660
tttacctcac ctcagaattt cctcgtatag ttctagctgg taattttatt ctatttagac      720
taatgatatc acattttaa cattttaata tgaccatgac atactccaga tgtatatgat      780
tccattagag ttaaaaatca tttaaatatg tggaagtgac tattaatata ggacttcact      840
gtatattttc atgtctactg accataattc taaaaatata accccaagtt gctagtactt      900
tcagaaaaac gttgaggtga ggaaagccaa cgacagaggt gaatggagcc taggaagtat      960
ctctgaccca atatggaatt cttttggaaa gaatgcctga cacgaggctc tttgagatgg     1020
agaactgaca acatcaaaaa agggcctgat ccacttgctt aatggattct acttaatatt     1080
gtagagccat tcctaacacc attcctaata ttcataagca cataatttac atccgcacac     1140
ataaaaacaa aatagataaa attaaatcat cccaatgtta actgatactt tatagcttaa     1200
aatatgaaac tgattcatgt aatcattta tcaaatcata atttaactta cattttatt     1260
ttcaggagta ggaatcatca ggttctgaaa aagaaaggaa acaacattca ttttaatgt     1320
attgtaaggt tcataacttt taatataatt cttctgagta acatggttac ccatttatat     1380
attattaaca ctcattactt cattattgat aatggatctt taaaaactag ccaccaccac     1440
caattaccca tgcattttaa agactgtagg aatcaaaaag aaaattaccc catcgcctat     1500
cagccaagtt cgatgagtgg agagcagtgt caaggtctct gccaccagtc tattcatggg     1560
atttctaca gcaaaggcag aaacataggc agccccaaga gctagcaaac tcaaattcag     1620
aagcattgtc atagctctga aatgttcagt gtttgcct                             1658
```

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: N-terminal
      peptide <400> SEQUENCE: 20

Phe Ala Val Glu Asn Pro Met Asn Arg Leu Val Ala Glu Thr Leu
 1               5                  10                  15

<210> SEQ ID NO 21
<211> LENGTH: 671
<212> TYPE: DNA
<213> ORGANISM: Canis familiaris
<400> SEQUENCE: 21

```
aggcaaacac tgaacatttc agagctatga gaatgcttct gaatttgagt ttgctagctc       60
ttggggctgc ctatgtttct gcctttgctg tagaaaatcc catgaataga ctggtggcag      120
agaccttgac actgctctcc actcatcgaa cttggctgat aggcgatggg gtaattttct      180
ttttgattcc tacagtcttt aaaatgcatg ggtaattggg gtggtggct agttttaaa       240
gatccattat caataatgaa gtaatgagtg ttaataatat ataatgggta accatgttac      300
```

-continued

```
tcagaagaat tatattaaaa gttatgaacc ttacaataca ttaaaaatga atgttgtttc    360
ctttcttttt cagaacctga tgattcctac tcctgaaaat aaaaatcacc aactgtgcat    420
taaagaagtt tttcagggta tagacacatt gaagaaccaa actgcccacg gggaggctgt    480
ggataaacta ttccaaaact tgtctttaat aaaagaacac atagagcgcc aaaaaaaaag    540
gtgtgcagga gaaagatgga gagtgacaaa gttcctagac tacctgcaag tatttcttgg    600
tgtaataaac accgagtgga caccggaaag ttgagaacaa accggcttat tgtagtggaa    660
gattttggag a                                                        671
```

US 7,427,661 B2

CANINE IL-5 PROTEINS AND FRAGMENTS THEREOF

CROSS-REFERENCE TO RELATED APPLICATIONS

This is a divisional of U.S. patent application Ser. No. 10/787,382, filed Feb. 24, 2004, now U.S. Pat. No. 7,183,080 entitled "CANINE IL-5 NUCLEIC ACID MOLECULES"; which is a continuation of U.S. patent application Ser. No. 09/755,633, filed Jan. 5, 2001, entitled "CANINE AND FELINE IMMUNOREGULATORY PROTEINS, NUCLEIC ACID MOLECULES, AND USES THEREOF", now abandoned, which is a continuation-in-part of U.S. patent application Ser. No. 09/322,409, filed May 28, 1999, now U.S. Pat. No. 6,471,957, entitled "CANINE IL-4 IMMUNOREGULATORY PROTEINS AND USES THEREOF"; which claims priority to U.S. Provisional Patent Application Ser. No. 60/087,306, filed May 29, 1998, entitled "CANINE INTERLEUKIN-4 AND FLT-3 LIGAND PROTEINS, NUCLEIC ACID MOLECULE AND USES THEREOF".

FIELD OF THE INVENTION

The present invention relates to canine interleukin-5 nucleic acid molecules, proteins encoded by such nucleic acid molecules, antibodies raised against such proteins and/or inhibitors of such proteins or nucleic acid molecules. The present invention also includes therapeutic compositions comprising such nucleic acid molecules, proteins, antibodies and/or inhibitors, as well as their use to regulate an immune response in an animal.

BACKGROUND OF THE INVENTION

Regulating immune responses in animals is important in disease management. Immune responses can be regulated by modifying the activity of immunoregulatory molecules and immune cells.

Several immunoregulatory molecules have been found in humans and other mammal species. Interleukin-4, produced by activated type 2 helper cells ($T_H2$ cells), has a number of functions. These functions include promotion of naive T cells and B cells to differentiate and proliferate. IL-4 promotes $T_H2$ differentiation and inhibits $T_H1$ development. FMS-like tyrosine kinase 3, (Flt-3 ligand) stimulates the expansion and mobilization of hematopoetic precursor cell stimulating activity. CD40 is a type I transmembrane protein expressed on antigen presenting cells, such as B lymphocytes, and other types of cells such as endothelial cells, epithelial cells, and fibroblasts. CD40 ligand (also known as CD154) is a type II transmembrane protein that is preferentially expressed on activated T lymphocytes. The CD40-CD154 interaction regulates diverse pathways of the immune system, including B cell proliferation, immunoglobulin production and class switching by B cells, activation and clonal expansion of T cells, activity of antigen presenting cells, growth and differentiation of epithelial cells, and regulation of inflammatory responses at mucosal and cutaneous sites. Interleukin-5 is produced by activated type 2 helper cells ($T_H2$), mast cells, and eosinophils. Its main functions include promotion of growth and differentiation of eosinophils and generation of cytotoxic T cells from thymocytes. Interleukin-13 is produced by $T_H1$ and $T_H2$ cells, and promotes growth and differentiation of B cells, up-regulation of MHC class II and CD23 expression on monocytes/macrophages and B cells; and inhibition of production of inflammatory cytokines such as IL-1α, IL-1β, IL-6, IL-8, IL-10, IL-12, among others. Interferon alpha is an antiviral protein that has three major functions: it inhibits viral replication by activating cellular genes that destroy mRNA and inhibit protein translation, it induces MHC class I expression in non virally-infected cells, increasing resistance to NK cells, and can activate NK cells. GM-CSF, (granulocyte-macrophage colony-stimulating factor) stimulates the production of granulocytes and macrophages.

Prior investigators have disclosed sequences encoding feline IL-4 (Lerner et al, Genbank Accession No. U39634); porcine IL-4 (Zhou et al., Genbank Accession No. L12991); bovine IL-4 (Heussler, V. T., et al., Gene. vol. 114, pp. 273-278, 1992); ovine IL-4 (Seow, H.-F., et al., Gene, vol. 124, pp. 291-293, 1993); human IL-4 (Yokota, T., et al., Proc. Natl. Acad. Sci. U.S.A., vol. 83(16), pp. 5894-5898, 1986); and murine IL-4 (Sideras, P., et al., Adv. Exp. Med. Biol., vol. 213, pp. 227-236, 1987). Prior investigators have disclosed sequences encoding murine Flt-3 ligand (McClanahan et al., Genbank Accession No. U44024); and human Flt-3 ligand (Lyman et al., Blood, vol. 83, pp. 2795-2801, 1994). Prior investigators have disclosed sequences encoding human CD40 (Stamenkovic et al., EMBO J., vol. 8:1403-1410, 1989, Genbank Accession No. (X60592), bovine CD40 (Hirano et al., Immunology, vol. 90, pp. 294-300, 1997, GenBank Accession No. U57745), and murine CD40 (Grimaldi et al., J. Immunol., vol. 143, pp. 3921-3926. 1992; Torres and Clark, J. Immunol., vol. 148, pp. 620-626, 1992, GenBank Accession No. M83312). Prior investigators have disclosed sequences encoding human CD154 (Graf et al., Eur. J. Immunol., vol. 22, pp. 3191-3194, 1992; Hollenbaugh, et al., EMBO J., vol. 11:4313-4321, 1992; Gauchat et al., FEBS lett., vol., 315, pp. 259-266, 1993; GenBank Accession Nos L07414, X68550, Z15017, X67878, respectively); bovine CD154 (Mertens et al., Immunogenetics, vol. 42, pp. 430-431, GenBank Accession No. Z48468); and murine CD154 (Armitage et al., Nature, vol. 357, pp. 80-82; 1992, GenBank Accession No. X65453). Prior investigators have disclosed sequences encoding feline interleukin-5 (Padrid et al., Am. J. Vet. Res., vol. 59, pp. 1263-1269, 1998, GenBank Accession No. AF025436) and human interleukin-5 (Azuma et al., Nucleic Acids Res., vol. 14, pp. 9149-9158, 1986, GenBank Accession No. X04688). Prior investigators have disclosed sequences encoding human interleukin-13 (McKenzie et al., Proc. Natl. Acad. Sci. USA, vol. 90, pp. 3735-3739, 1993; Minty et al., Nature, vol. 362, pp. 248-250, 1993, GenBank Accession Nos L06801 and X69079, respectively); murine interleukin-13 (Brown et al., J. Immunol., vol. 142, pp. 679-687, 1989, GenBank Accession No M23504); and rat interleukin-13 (Lakkis et al., Biochem. Biophys. Res. Commun., Vol. 197, pp. 612-618, 1993, GenBank Accession No. L26913). Prior investigators have disclosed sequences encoding feline interferon (Nakamura; N., Sudo, T., Matsuda, S., Yanai, A., Biosci. Biotechnol. Biochem. (1992) Vol: 56 pp 211-214, GenBank accession # E02521). Prior investigators have also disclosed sequences encoding feline GM-CSF (direct submission to GenBank, Accession No. AF053007)

There remains a need for compounds and methods to regulate an immune response by manipulation of the function of canine interleukin-5.

SUMMARY OF THE INVENTION

The present invention relates to canine interleukin-5 nucleic acids, proteins encoded by such nucleic acid molecules, antibodies raised against such proteins and/or inhibitors of such proteins or nucleic acid molecules. Identification of the nucleic acid molecules of the present invention is unexpected because initial attempts to obtain nucleic acid molecules using PCR were unsuccessful. After numerous attempts, the inventors discovered specific primers that were useful for isolating such nucleic acid molecules.

One embodiment of the invention is an isolated nucleic acid molecule comprising a nucleic acid sequence selected from the group consisting of SEQ ID NO:18 and SEQ ID NO:19, and/or a homolog thereof, wherein said homolog has an at least 45 contiguous nucleotide region identical in sequence to a 45 contiguous nucleotide region of a nucleic acid molecule having a nucleic acid sequence selected from the group consisting of SEQ ID NO:18 and SEQ ID NO:19.

A second embodiment of the present invention is a nucleic acid molecule having a nucleic acid sequence that is at least about 90 percent identical to a nucleic acid sequence selected from the group consisting of SEQ ID NO:18 and SEQ ID NO:19.

The present invention also includes methods to produce any of the proteins of the present invention using nucleic acid molecules of the present invention and recombinantly using such nucleic acid molecules.

One aspect of the present invention is a therapeutic composition that, when administered to an animal, regulates an immune response in said animal, said therapeutic composition comprising a therapeutic compound selected from the group consisting of: an immunoregulatory protein of the present invention; a mimetope of any of said immunoregulatory proteins; and a multimeric form of any of said immunoregulatory proteins; an isolated nucleic acid molecule of the present invention; an antibody that selectively binds to any of said immunoregulatory proteins; and/or an inhibitor of a immunoregulatory protein activity identified by its ability to inhibit the activity of any of said immunoregulatory proteins. Yet another aspect of the present invention is a method to regulate an immune response in an animal comprising administering to the animal a therapeutic composition of the present invention.

The present invention also includes a method to produce an immunoregulatory protein, said method comprising culturing a cell capable of expressing said protein, said protein being encoded by a nucleic acid molecule of the present invention.

One embodiment of the present invention is a method to identify a compound capable of regulating an immune response in an animal, said method comprising: contacting an isolated canine IL-5 protein of the present invention with a putative inhibitory compound under conditions in which, in the absence of said compound, said protein has TF-1 cell proliferation activity; and determining if said putative inhibitory compound inhibits said activity.

DETAILED DESCRIPTION OF THE INVENTION

The present invention provides for isolated canine interleukin-5 proteins, isolated canine interleukin-5 nucleic acid molecules, antibodies directed against canine interleukin-5 protein, and compounds derived therefrom that regulate the immune response of an animal (e.g. inhibitors, antibodies and peptides).

Canine IL-5 can refer to canine IL-5, including homologs thereof. As used herein, the phrase "regulate an immune response" refers to modulating the activity of cells or molecules involved in an immune response. The term "regulate" can refer to increasing or decreasing an immune response. Regulation of an immune response can be determined using methods known in the art as well as methods disclosed herein.

The term, "immunoregulatory protein" refers to a protein that can modulate the activity of cells or of molecules involved in an immune response. An immunoregulatory protein of the present invention refers to a canine IL-5 protein as described herein. As used herein, the terms isolated canine interleukin-5 nucleic acid molecules refer to canine interleukin-5 nucleic acid molecules derived from mammals and, as such, can be obtained from their natural source, or can be produced using, for example, recombinant nucleic acid technology or chemical synthesis. Also included in the present invention is the use of these proteins, nucleic acid molecules, antibodies, and/or compounds derived therefrom as therapeutic compositions to regulate the immune response of an animal as well as in other applications, such as those disclosed below.

One embodiment of the present invention is an isolated protein that includes a canine interleukin-5 protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and/or "biologically pure" do not necessarily reflect the extent to which the protein has been purified. An isolated protein of the present invention can be obtained from its natural source, can be produced using recombinant DNA technology, or can be produced by chemical synthesis. Nucleic acid molecules of the present invention of known length isolated from *Canis familiaris* are denoted as follows: IL-5 is denoted as nCaIL-$5_x$, for example, nCaIL-$5_{610}$, wherein "#" refers to the number of nucleotides in that molecule. Similarly, proteins of the present invention of known length isolated from *Canis familiaris* are denoted PCaIL-$5_x$.

As used herein, an isolated canine interleukin-5 protein of the present invention can be a full-length protein or any homolog of such a protein. An isolated IL-5 protein of the present invention, including a homolog, can be identified in a straight-forward manner by the protein's ability to elicit an immune response to an IL-5 protein, bind to an L-5 receptor, and/or stimulate eosinophils and/or cause thymocytes to produce cytotoxic T cells.

Examples of protein homologs of the present invention include immunoregulatory proteins of the present invention in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the protein homolog includes at least one epitope capable of eliciting an immune response against the parent protein, of binding to an antibody directed against the parent protein and/or of binding to the parent's receptor, where the term parent refers to the longer and/or full-length protein that the homolog is derived from. That is, when the homolog is administered to an animal as an immunogen, using techniques known to those skilled in the art, the animal will produce an immune response against at least one epitope of an immunoregulatory protein of the present invention, depending upon which protein is administered to an animal. The ability of a protein to effect an immune response can be measured using techniques known to those skilled in the art. As used herein, the term "epitope" refers to the smallest portion of a protein capable of selectively binding to the antigen binding site of an antibody. It is well accepted by those skilled in the art that the minimal size of a protein epitope capable of selectively binding to the antigen binding site of an antibody is about five or six to seven amino acids.

Homologs of immunoregulatory proteins of the present invention can be the result of natural allelic variation, including natural mutation. Protein homologs of the present invention can also be produced using techniques known in the art including, but not limited to, direct modifications to the protein and/or modifications to the gene encoding the protein using, for example, classic or recombinant DNA techniques to effect random or targeted mutagenesis.

Immunoregulatory proteins of the present invention include variants of a full-length protein of the present invention. Such variants include proteins that are less than full-length. As used herein, variants of the present invention refer to nucleic acid molecules that are naturally-occurring as defined below, and may result from alternative RNA splicing, alternative termination of an amino acid sequence or DNA recombination. Examples of variants include allelic variants as defined below. It is to be noted that a variant is an example of a homolog of the present invention.

Immunoregulatory proteins of the present invention are encoded by nucleic acid molecules of the present invention. As used herein, an IL-5 nucleic acid molecule includes nucleic acid sequences related to a natural IL-5 gene. As used herein, a canine IL-5 gene refers to the natural genomic elements that encode a canine IL-5 protein, and includes all regions such as regulatory regions that control production of the protein encoded by the gene (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that region that is translated into a full-length, i.e., a complete, protein as would be initially translated in its natural milieu, prior to any post-translational modifications.

In another embodiment, an IL-5 gene of the present invention includes the nucleic acid sequence SEQ ID NO:18, as well as the complement represented by SEQ ID NO: 19.

Additional immunoregulatory nucleic acid molecules and proteins of the present invention having specific sequence identifiers are described in Table 1.

TABLE 1

Sequence identification numbers (SEQ ID NOs) and their corresponding nucleic acid molecules or proteins.

| SEQ ID Nos | DESCRIPTION |
|---|---|
| 1 | primer (m) ATGCACTTT . . . |
| 2 | primer (n) CTGGAGGAA . . . |
| 3 | primer (o) GTGACYCTT |
| 4 | nCaIL-5$_{610}$    CDS 29-430 |
| 5 | PCaIL-5$_{134}$ |
| 6 | reverse complement for nCaIL-5$_{610}$ |
| 7 | nCaIL-5$_{402}$ (coding for PCaIL-5$_{134}$) |
| 8 | reverse complement of nIL-5$_{402}$ |

TABLE 1-continued

Sequence identification numbers (SEQ ID NOs) and their corresponding nucleic acid molecules or proteins.

| SEQ ID Nos | DESCRIPTION |
|---|---|
| 9 | nCaIL-5$_{345}$ (mature sequence) CDS 1-345 |
| 10 | PCaIL-5$_{115}$ (mature protein) |
| 11 | reverse complement of nCaIL-5$_{345}$ |
| 12 | primer (p) GGGCTCGAG . . . |
| 13 | primer (q) CCCGCGGCC |
| 14 | 5' AGGCAAACACTGAACATTTC3' |
| 15 | 5'TCTCCAAAATCTTCCACTAC3' |
| 16 | 5'TCAAGGGAGGCTATAAATTC3' |
| 17 | 5'TTATAGTCAAGGGCATATCC3' |
| 18 | nCAIL-5$_{1658}$ |
| 19 | reverse complement of SEQ ID NO:18 |
| 20 | N-terminal amino acid sequence |
| 21 | partially processed transcript |

In another embodiment, an IL-5 gene or nucleic acid molecule can be an allelic variant that includes a similar but not identical sequence to SEQ ID NO:18 and SEQ ID NO:19, and/or any other IL-5 nucleic acid sequence cited herein.

An allelic variant of a canine interleukin-5, including the particular SEQ ID NO's cited herein, is a gene that occurs at essentially the same locus (or loci) in the genome as the gene including the particular SEQ ID NO's cited herein, but which, due to natural variations caused by, for example, mutation or recombination, has a similar but not identical sequence. Also included in the term allelic variant are allelic variants of cDNAs derived from such genes. Because natural selection typically selects against alterations that affect function, allelic variants usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found within a given animal, since the respective genomes are diploid, and sexual reproduction will result in the reassortment of alleles.

The minimal size of an canine interleukin-5 protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267-284, each of which is incorporated herein by this reference. As explained in detail in the cited references, the determination of hybridization conditions involves the manipulation of a set of variables including the ionic strength (M, in moles/liter), the hybridization temperature (° C.), the concentration of nucleic acid helix destabilizing agents, such as formamide, the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5°\text{ C.} + 16.6 \log M + 0.41(\% G+C) - 500/n - 0.61(\% \text{ formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions, by altering, for example, the salt concentration, the formamide concentration or the temperature, so that only nucleic acid hybrids with greater than a specified % base pair mismatch will hybridize. Stringent hybridization conditions are commonly understood by those skilled in the art to be those experimental conditions that will allow about 30% base pair mismatch, i.e., about 70% identity. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene or specified nucleic acid molecule under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

Preferred portions, or fragments, of a canine interleukin-5 protein of the present invention include at least 15 amino acids, at least 20 amino acids, at least 25 amino acids, at least 30 amino acids, at least 35 amino acids, at least 40 amino acids, at least 45 amino acids, at least 50 amino acids, at least 60 amino acids, at least 75 amino acids or at least 100 amino acids. An IL-5 protein of the present invention can include at least a portion of an IL-5 protein that is capable of binding to an IL-5 receptor. IL-5 receptors are known to those of skill in the art, and are described in Janeway et al., in *Immunobiology, the Immune System in Health and Disease*, Garland Publishing, Inc., NY, 1996 (which is incorporated herein by this reference in its entirety). The IL-5 receptor-binding portion of an IL-5 protein, can be determined by incubating the protein with an isolated IL-5 receptor, or a cell having an IL-5 receptor on its surface. IL-5 protein binding to purified IL-5 receptor, can be determined using methods known in the art including Biacore® screening, confocal immunofluorescent microscopy, immunoprecipitation, gel chromatography, determination of inhibition of binding of antibodies that bind specifically to the IL-5 binding domain of an IL-5 receptor, ELISA using an IL-5 receptor, labeled with a detectable tag such as an enzyme or chemiluminescent tag or yeast-2 hybrid technology.

The present invention also includes mimetopes of canine interleukin-5 proteins of the present invention. As used herein, a mimetope of an immunoregulatory protein of the present invention refers to any compound that is able to mimic the activity of such a canine interleukin-5 protein, often because the mimetope has a structure that mimics the particular protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and/or synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of an immunoregulatory protein of the present invention is a fusion protein that includes a canine interleukin-5 protein-containing domain, attached to one or more fusion segments. Suitable fusion segments for use with the present invention include, but are not limited to, segments that can: link two or more immunoregulatory proteins of the present invention, to form multimeric forms of an immunoregulatory protein of the present invention; enhance a protein's stability; act as an immunopotentiator to enhance an immune response against an canine interleukin-5 protein; and/or assist in purification of a canine interleukin-5 protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the IL-5-containing domain of a protein and can be susceptible to cleavage in order to enable straight-forward recovery of either canine interleukin-5 protein. Fusion proteins are preferably produced by culturing a recombinant cell transformed with a fusion nucleic acid molecule that encodes a protein including the fusion segment attached to either the carboxyl and/or amino terminal end of a canine interleukin-5-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of -galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

A suitable fusion segment that links one IL-5 protein to another IL-5 protein, and includes any amino acid sequence that enables such proteins to be linked while maintaining the biological function of the canine interleukin-5 protein. Selection of a suitable linker is dependent upon how many proteins are to be linked to form one multimeric molecule, and from where on either the canine interleukin-5 molecule the linker extends. Preferably, a linker fusion segment of the present invention comprises a peptide of from about 6 amino acid residues to about 40 residues, more preferably from about 6 residues to about 30 residues in length.

In another embodiment, an canine interleukin-5 protein of the present invention also includes at least one additional protein segment that is capable of targeting canine interleukin-5 protein, to a desired cell or receptive molecule. Such a multivalent targeting protein can be produced by culturing a cell transformed with a nucleic acid molecule comprising two or more nucleic acid domains joined together in such a manner that the resulting nucleic acid molecule is expressed as a multivalent targeting protein containing a canine interleukin-5 protein or portion thereof and/or at least one targeting compound capable of delivering the canine interleukin-5 protein to a desired site in an animal.

Examples of multivalent targeting proteins include, but are not limited to, a canine interleukin-5 protein of the present invention attached to one or more compounds that can bind to a receptive molecule on the surface of a cell located in an area of an animal where regulation of an immune response is desired. One of skill in the art can select appropriate targeting fusion segments depending upon the cell or receptive molecule being targeted.

Another example of a multivalent protein of the present invention includes, but is not limited to, a canine interleukin-5 protein of the present invention attached to one or more proteins that are potentially antigenic in mammals. Thus, immunogenicity of the potentially antigenic protein could be enhanced by administering to a mammal together with an immunoregulatory protein of the present invention.

A naturally-occurring variant of a canine interleukin-5 protein of the present invention is preferably isolated from (including isolation of the natural protein or production of the protein by recombinant or synthetic techniques) from mammals, including but not limited to dogs (i.e., canids), cats (i.e., felids), horses (i.e., equids), humans, cattle, chinchillas, ferrets, goats, mice, minks, rabbits, raccoons, rats, sheep, squirrels, swine, chickens, ostriches, quail and/or turkeys as well as other furry animals, pets, zoo animals, work animals and/or food animals. Particularly preferred animals from which to isolate canine interleukin-5 proteins are dogs, cats, horses and/or humans.

A preferred isolated protein of the present invention is an isolated protein that is encoded by a nucleic acid molecule the having nucleic acid sequence SEQ ID NO:18 and SEQ ID NO:19, and/or an allelic variant of such a nucleic acid molecule.

Translation of SEQ ID NO:4, the coding strand for nCaIL-$5_{610}$, yields a protein of about 134 amino acids, denoted herein as PCaIL-$5_{134}$, the amino acid sequence of which is presented in SEQ ID NO:5, assuming an open reading frame having an initiation codon spanning from nucleotide 29 through nucleotide 31 of SEQ ID NO:4, and a stop codon spanning from nucleotide 431 through nucleotide 433 of SEQ ID NO:4.

Preferred IL-5 proteins of the present invention includes proteins that are at least about 85% identical, even more preferably at least about 90%, and even more preferably at least about 95% identical to PCaIL-$5_{134}$, PCaIL-$5_{115}$ and/or fragments thereof.

More preferred are IL-5 proteins comprising PCaIL-$5_{134}$, PCaIL-$5_{115}$, and/or proteins encoded by allelic variants of a nucleic acid molecule encoding one of the proteins PCaIL-$5_{134}$ and/or PCaIL-$5_{115}$.

Preferred IL-5 proteins of the present invention includes proteins that are at least about 85% identical, even more preferably at least about 90%, and even more preferably at least about 95% identical to SEQ ID NO:5, SEQ ID NO:10 and/or fragments thereof.

More preferred are IL-5 proteins comprising SEQ ID NO:5, SEQ ID NO:10 and/or proteins encoded by allelic variants of a nucleic acid molecule encoding one of the proteins SEQ ID NO:5, and/or SEQ ID NO:10.

Percent identities between amino acid or nucleic acid sequences can be determined using standard methods known to those of skill in the art. It is known in the art that methods to determine the percentage identity and the number of gaps are substantially similar when different methods for determining sequence similarity are used and when the degree of similarity is greater than 30% amino acid identity, as described by Johnson et al., *J. Mol. Biol.*, vol. 233, pages 716-738, 1993, and Feng et al., *J. Mol. Evol.*, vol. 21, pages 112-125, 1985, which are incorporated by reference herein in their entirety. Preferred methods to determine percentage identities between amino acid sequences and between nucleic acid sequences include comparisons using various computer programs such as GCG™ program (available from Genetics Computer Group, Madison, Wis.), DNAsis™ program (available from Hitachi Software, San Bruno, Calif.) or the MacVector™ program (available from the Eastman Kodak Company, New Haven, Conn.). Preferred settings for sequence comparisons using the DNAsis™ computer program or the GAP GCG™ program are disclosed herein in the Examples section.

Additional preferred IL-5 proteins of the present invention include proteins encoded by nucleic acid molecules encoding at least a portion of nCaIL-$5_{610}$, nCaIL-$5_{402}$, nCaIL-$5_{345}$ and/or nCaIL-$5_{1658}$ as well as IL-5 proteins encoded by allelic variants of such nucleic acid molecules.

Also preferred are IL-5 proteins encoded by nucleic acid molecules having nucleic acid sequences comprising at least a portion of SEQ ID NO:4, SEQ ID NO:7, and/or SEQ ID NO:9, as well as allelic variants of these nucleic acid molecules.

Another embodiment of the present invention is a canine interleukin-5 nucleic acid molecule that includes one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a canine interleukin-5 nucleic acid molecule of the present invention is from about 12 to about 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated canine interleukin-5 nucleic acid molecule of the present invention can be isolated from its natural source or produced using recombinant DNA technology (e.g., polymerase chain reaction (PCR) amplification or cloning) or chemical synthesis. Isolated canine interleukin-5 nucleic acid molecules can include, for example, natural allelic variants and/or nucleic acid molecules modified by nucleotide insertions, deletions, substitutions, and/or inversions in a manner such that the modifications do not substantially interfere with the nucleic acid molecule's ability to encode an canine interleukin-5 protein of the present invention.

A canine interleukin-5 ligand nucleic acid molecule homolog can be produced using a number of methods known to those skilled in the art, see, for example, Sambrook et al., 1989, *Molecular Cloning: A Laboratory Manual*, Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with a canine interleukin-5 nucleic acid molecule or by screening the function of a protein encoded by the nucleic acid molecule (e.g., ability to elicit an immune response against at least one epitope of a canine interleukin-5 protein).

An isolated nucleic acid molecule of the present invention can include a nucleic acid sequence that encodes at least one canine interleukin-5 protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a canine interleukin-5 protein.

A preferred nucleic acid molecule of the present invention, when administered to an animal, is capable of regulating an immune response in an animal. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode an immunoregulatory protein (e.g., a cell-bound or soluble protein of the present invention), the nucleic acid molecule being delivered to the animal, for example, by direct injection (i.e, as a genetic vaccine) or in a vehicle such as a recombinant virus vaccine or a recombinant cell vaccine.

One embodiment of the present invention is an IL-5 nucleic acid molecule comprising all or part of nucleic acid molecules nCaIL-$5_{610}$, nCaIL-$5_{402}$, nCaIL-$5_{345}$, and/or nCaIL-$5_{1658}$ and/or allelic variants of these nucleic acid molecules. Another preferred nucleic acid molecule of the present invention includes at least a portion of (i.e., a fragment of the nucleic acid molecule) nucleic acid sequence SEQ ID NO:4, SEQ ID NO:6, SEQ ID NO:7, SEQ ID NO:8, SEQ ID NO:9, SEQ ID NO:11, SEQ ID NO:18 and SEQ ID NO:19, as well as allelic variants of nucleic acid molecules having these nucleic acid sequences. Such nucleic acid molecules can include nucleotides in addition to those included in the SEQ ID NOs, such as, but not limited to, a full-length gene, a full-length coding region, a nucleic acid molecule encoding a fusion protein, and/or a nucleic acid molecule encoding a multivalent therapeutic compound.

One embodiment of an isolated nucleic acid molecule of the present invention is a nucleic acid molecule that can be any of the following: an isolated nucleic acid molecule comprising a nucleic acid sequence selected from the group consisting of SEQ ID NO:4, SEQ ID NO:6, SEQ ID NO:7, SEQ ID NO:8, SEQ ID NO:9, SEQ ID NO:11, SEQ ID NO: 18 and/or SEQ ID NO:19, and/or a homolog thereof, wherein said homolog has an at least 45 contiguous nucleotide region identical in sequence to a 45 contiguous nucleotide region of a nucleic acid molecule having a nucleic acid sequence selected from the group consisting of SEQ ID NO:4, SEQ ID NO:6, SEQ ID NO:7, SEQ ID NO:8, SEQ ID NO:9, SEQ ID NO:11, SEQ ID NO:18, and/or SEQ ID NO:19. The phrase, a homolog having an at least "x" contiguous nucleotide region identical in sequence to an "x" contiguous nucleotide region of a nucleic acid molecule selected from the group consisting of SEQ ID NO:"y", refers to an "x"-nucleotide in length nucleic acid molecule that is identical in sequence to an "x"-nucleotide portion of SEQ ID NO:"y", as well as to nucleic acid molecules that are longer in length than "x". The additional length may be in the form of nucleotides that extend from either the 5' or the 3' end(s) of the contiguous identical "x"-nucleotide portion. The 5' and/or 3' extensions can include one or more extensions that have no identity to an immunoregulatory molecule of the present invention, as well as extensions that show similarity or identity to cited nucleic acids sequences or portions thereof.

In another embodiment, an isolated nucleic acid molecule of the present invention can be any of the following: a nucleic acid molecule having a nucleic acid sequence encoding an IL-5 protein selected from the group consisting of (i) a protein having an amino acid sequence that is at least about 85 percent identical to an amino acid sequence selected from the group consisting of SEQ ID NO:5 and/or SEQ ID NO:10 and/or (ii) a protein comprising a fragment of at least 20 amino acids of an amino acid sequence selected from the group consisting of SEQ ID NO:5 and/or SEQ ID NO:10, wherein said IL-5 protein elicits an immune response against a IL-5 protein selected from the group consisting of SEQ ID NO:5 and/or SEQ ID NO:10 and/or is a protein with IL-5 activity.

In one embodiment, an IL-5 nucleic acid molecule of the present invention encodes a protein that is at least about 85%, more preferably at least about 90%, and even more preferably at least about 95% identical to PCaIL-$5_{134}$, and/or PCaIL-$5_{115}$.

In another embodiment, an IL-5 nucleic acid molecule of the present invention encodes a protein having an amino acid sequence that is at least about at least about 85%, at least about 85%, more preferably at least about 90%, and even more preferably at least about 95% identical to SEQ ID NO:5 and/or SEQ ID NO:10. The present invention also includes an IL-5 nucleic acid molecule encoding a protein having at least a portion of SEQ ID NO:5 and/or SEQ ID NO: 10, as well as allelic variants of an IL-5 nucleic acid molecule encoding a protein having these sequences, including nucleic acid molecules that have been modified to accommodate codon usage properties of the cells in which such nucleic acid molecules are to be expressed.

In one embodiment, an IL-<nucleic acid molecule of the present invention is at least about 90% and preferably at least about 95% identical to $nCaIL-5_{610}$, $nCaIL-5_{402}$, $nCaIL-5_{345}$, and $nCaIL-5_{1658}$ and/or an allelic variant of such a nucleic acid molecule.

In one embodiment, an IL-5 nucleic acid molecule of the present invention comprises a nucleic acid sequence that is at least about 90% and preferably at least about 95% identical to SEQ ID NO:4, SEQ ID NO:6, SEQ ID NO:7, SEQ ID NO:8, SEQ ID NO:9, SEQ ID NO:11, SEQ ID NO:18 and/or SEQ ID NO:19. The present invention also includes an IL-5 nucleic acid molecule comprising at least a portion of SEQ ID NO:4, SEQ ID NO:6, SEQ ID NO:7, SEQ ID NO:8, SEQ ID NO:9, SEQ ID NO:11, SEQ ID NO:18 and/or SEQ ID NO:19, as well as allelic variants of such IL-5 nucleic acid molecules, including nucleic acid molecules that have been modified to accommodate codon usage properties of the cells in which such nucleic acid molecules are to be expressed.

Knowing the nucleic acid sequences of certain immunoregulatory nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and/or (c) obtain other immunoregulatory nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include mammalian cDNA libraries as well as genomic DNA libraries. Similarly, preferred DNA sources from which to amplify nucleic acid molecules include mammalian cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising canine interleukin-5 nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of about 100 nucleotides. The present invention includes oligonucleotides that can be used as, for example, probes to identify nucleic acid molecules, primers to produce nucleic acid molecules, or therapeutic reagents to inhibit canine interleukin-5 protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating immunoregulatory nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein, more preferably in vivo.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth and/or other endoparasite, insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with mammals, such as dog, cat, horse or human transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nCaIL-5_{610}$, $nCaIL-5_{402}$, $nCaIL-5_{345}$, and $nCaIL-5_{1658}$.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include immunoregulatory nucleic acid molecules of the present invention disclosed herein. Particularly preferred nucleic acid molecules with which to transform a cell include $nCaIL-5_{610}$, $nCaIL-5_{402}$, $nCaIL-5_{345}$, and/or $nCaIL-5_{1658}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing immunoregulatory proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include *Salmonella, Escherichia, Bacillus, Listeria, Saccharomyces, Spodoptera, Mycobacteria, Trichoplusia*, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, chinese hamster ovary (CHO) cells, Ltk cells and Vero cells. Particularly preferred host cells are *Escherichia coli*, including *E. coli* K-12 derivatives; *Salmonella typhi; Salmonella typhimurium*, including attenuated strains such as UK-1 $_0$3987 and SR-11 $_0$4072; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including any of canine interleukin-5 nucleic acid molecule encoding one or more proteins of the present invention and/or one or more other nucleic acid molecules encoding other therapeutic compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated immunoregulatory proteins of the present invention can be produced in a variety of ways, including production and/or recovery of natural proteins, production and/or recovery of recombinant proteins, and/or chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an immunoregulatory protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and/or differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to an immunoregulatory protein of the present invention and/or a mimetope thereof (e.g., anti-IL-5 antibodies). As used herein, the term "selectively binds to" an immunoregulatory protein of the present invention, refers to the ability of antibodies of the present invention to preferentially bind to specified proteins and/or mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by this reference herein in its entirety. An anti-IL-5 antibody of the present invention preferably selectively binds to an IL-5 protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and/or genetically-engineered antibodies, including single chain antibodies or chimeric antibodies that can bind to one or more epitopes.

A preferred method to produce antibodies of the present invention includes (a) administering to an animal an effective amount of a protein, peptide and/or mimetope thereof of the present invention to produce the antibodies and (b) recovering the antibodies. In another method, antibodies of the present invention are produced recombinantly using techniques as heretofore disclosed to produce any of the immunoregulatory proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as reagents in assays to detect an immunoregulatory protein of the present invention, (b) as reagents in assays to modulate cellular activity through an immunoregulatory protein of the present invention (e.g., mimicking ligand binding to a canine interleukin-5), and/or (c) as tools to screen expression libraries and/or to recover desired proteins of the present invention from a mixture of proteins and other contaminants. Furthermore, antibodies of the present invention can be used to target compounds (e.g., nucleic acid molecules, drugs or proteins) to antigen presenting cells. Targeting can be accomplished by conjugating (i.e., stably joining) such antibodies to the compounds using techniques known to those skilled in the art. Suitable compounds are known to those skilled in the art.

One embodiment of the present invention is a therapeutic composition that, when administered to an animal in an effective manner, is capable of regulating an immune response in an animal. Therapeutic compositions of the present invention can include at least one of the following therapeutic compounds: an isolated IL-5 protein of the present invention and/or a mimetope thereof; an isolated IL-5 nucleic acid molecule of the present invention; an isolated antibody that selectively binds to an IL-5 protein of the present invention; an inhibitor of canine IL-5 function identified by its ability to bind to an IL-5 protein, respectively, of the present invention; such an inhibitor can inhibit binding of the respective immunoregulatory protein with its respective receptor, or inhibit the activity the respective protein. Methods to perform such assays to measure binding and/or activity of an immunoregulatory protein of the present invention are known to those of skill in the art, and are described, for example, in Janeway et al., ibid. As used herein, a therapeutic compound refers to a compound that, when administered to an animal in an effective manner, is able to treat, ameliorate, and/or prevent a disease. Examples of proteins, nucleic acid molecules, antibodies and/or inhibitors of the present invention are disclosed herein.

The present invention also includes a therapeutic composition comprising at least one IL-5-based compound of the present invention in combination with at least one additional therapeutic compound. Examples of such compounds are disclosed herein.

Therapeutic compositions of the present invention can be administered to any animal susceptible to such therapy, preferably to mammals, and more preferably to dogs, cats, humans, ferrets, horses, cattle, sheep and/or other pets, economic food animals and/or zoo animals. Preferred animals include dogs, cats, horses and/or humans.

A therapeutic composition of the present invention is administered to an animal in an effective manner such that the composition is capable of regulating an immune response in that animal. Therapeutic compositions of the present invention can be administered to animals prior to onset of a disease (i.e., as a preventative vaccine) and/or can be administered to animals after onset of a disease in order to treat the disease (i.e., as a therapeutic vaccine). Preferred diseases to prevent and/or treat include autoimmune diseases, allergic reactions, infectious diseases, tumor development, inflammatory diseases and/or graft rejection. In one embodiment, a therapeutic composition of the present invention is administered with an antigen to enhance an immune response against that antigen.

Therapeutic compositions of the present invention can be formulated in an excipient that the animal to be treated can tolerate. Examples of such excipients include water, saline, Ringer's solution, dextrose solution, Hank's solution, and/or other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and/or Tris buffer, while examples of preservatives include thimerosal, o-cresol, formalin and/or benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and/or compounds that induce the production of cytokines and/or chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunters Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphere, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to regulate an immune response in an animal. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to and/or after onset of disease. Acceptable protocols to administer therapeutic compositions in an effective manner include individual dose size, number of doses, frequency of dose administration, and/or mode of administration. Determination of such protocols can be accomplished by those skilled in the art. A suitable single dose is a dose that is capable of regulating the immune response in an animal when administered one or more times over a suitable time period. For example, a preferred single dose of a protein, mimetope or antibody therapeutic composition is from about 1 microgram (µg) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 µg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intra nasal, intraoccular, oral, transdermal and/or intramuscular routes.

According to one embodiment, a nucleic acid molecule of the present invention can be administered to an animal in a fashion to enable expression of that nucleic acid molecule into a therapeutic protein or therapeutic RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465-1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxviruses, adenoviruses, herpesviruses, picornaviruses, and/or retroviruses, with those based on alphaviruses (such as sindbis or Semliki forest virus), species-specific herpesviruses and/or poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intra nasal and/or oral routes of administration being preferred. A preferred single dose of a genetic vaccine ranges from about 1 nanogram (ng) to about 600 μg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and/or retroviruses. Preferred recombinant virus vaccines are those based on alphaviruses (such as Sindbis virus), raccoon poxviruses, species-specific herpesviruses and/or species-specific poxviruses. An example of methods to produce and use alphavirus recombinant virus vaccines are disclosed in U.S. Pat. No. 5,766,602 by Xiong et al., issued Jun. 16, 1998, which is incorporated by reference herein in its entirety.

When administered to an animal, a recombinant virus vaccine of the present invention infects cells within the immunized animal and directs the production of a therapeutic protein or RNA nucleic acid molecule that is capable of protecting the animal from disease caused by a parasitic helminth as disclosed herein. For example, a recombinant virus vaccine comprising an immunoregulatory nucleic acid molecule of the present invention is administered according to a protocol that results in the regulation of an immune response in an animal. A preferred single dose of a recombinant virus vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intra nasal, intraoccular and/or oral administration routes being preferred.

A recombinant cell vaccine of the present invention includes recombinant cells of the present invention that express at least one protein of the present invention. Preferred recombinant cells for this embodiment include *Salmonella, E. coli, Listeria, Mycobacterium, S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to regulate the immune response in an animal can be tested in a variety of ways including, but not limited to, detection of cellular immunity within the treated animal, determining lymphocyte or dendritic cell activity, detection of immunoglobulin levels, determining hematopoietic stem cell or hematopoietic early progenitor cell development, determining dendritic cell development or challenge of the treated animal with an infectious agent to determine whether the treated animal is resistant to disease. In one embodiment, therapeutic compositions can be tested in animal models such as mice. Such techniques are known to those skilled in the art.

One embodiment of the present invention is an inhibitory compound. Preferably, such an inhibitory compound is derived from an IL-5 protein of the present invention. Examples of inhibitory compounds include an antibody of the present invention, that is administered to an animal in an effective manner (i.e., is administered in an amount so as to be present in the animal at a titer that is sufficient, upon interaction of that antibody with a native IL-5 protein, to decrease the activity of such proteins in an animal, at least temporarily). Oligonucleotide nucleic acid molecules of the present invention can also be administered in an effective manner, thereby reducing expression of an IL-5 protein, in order to interfere with the protein activity targeted in accordance with the present invention. Peptides of an IL-5 protein of the present invention can also be administered in an effective manner, thereby reducing binding of IL-5 proteins to the appropriate receptors in order to interfere with the protein activity targeted in accordance with the present invention. An inhibitory compound of an L-5 function can be identified using IL-5 proteins of the present invention.

Another embodiment of the present invention is a method to identify a compound capable of inhibiting IL-5 function. Such a method includes the steps of: (a) contacting an isolated IL-5 protein of the present invention, with a putative inhibitory compound under conditions in which, in the absence of the compound, the IL-5 protein binds to IL-5 receptor or stimulates T cells in a T cell proliferation assay, and (b) determining if the putative inhibitory compound inhibits the binding of IL-5 protein to IL-5 receptor or the stimulation of T cells in a T cell proliferation assay.

Putative inhibitory compounds to screen include small organic molecules, antibodies (including mimetopes thereof), and/or ligand analogs. Such compounds are also screened to identify those that are substantially not toxic in host animals.

Preferred IL-5 proteins to inhibit are those produced by dogs, cats, horses or humans, even more preferred IL-5 proteins to inhibit are those produced by domestic dogs or cats. A particularly preferred inhibitor of the present invention is capable of regulating an immune response in an animal. It is also within the scope of the present invention to use inhibitors of the present invention to target diseases involving undesired immune activity in animals. Compositions comprising inhibitors of IL-5 function can be administered to animals in an effective manner to regulate the immune response in the animals, and preferably to prevent autoimmune disease, allergy, infectious disease, inflammation or prevent graft rejection in animals, or to treat animals with such diseases. Effective amounts and/or dosing regimens can be determined using techniques known to those skilled in the art.

It is also within the scope of the present invention to use isolated proteins, mimetopes, nucleic acid molecules and/or antibodies of the present invention as diagnostic reagents. Methods to use such diagnostic reagents are well known to those skilled in the art, see, for example, Janeway, et al., ibid., and/or PCT Publication No. WO 98/23964, published Jun. 4, 1998, which is herein incorporated by reference.

The following examples are provided for the purposes of illustration and are not intended to limit the scope of the present invention.

EXAMPLES

It is to be noted that the examples include a number of molecular biology, microbiology, immunology and biochemistry techniques considered to be familiar to those skilled in the art. Disclosure of such techniques can be found, for example, in Sambrook et al., ibid. and Ausubel, et al., 1993, *Current Protocols in Molecular Biology*, Greene/Wiley Interscience, New York, N.Y., and related references. Ausubel, et al, ibid. is incorporated by reference herein in its entirety.

Example 1

This example describes the isolation and sequencing of certain canine IL-5 nucleic acid molecules and proteins of the present invention. This example also describes expression of canine IL-5 in a *Pichia* expression system.

A. Isolation and Sequencing of Canine IL-5 Nucleic Acid Molecules and Proteins

A canine IL-5 cDNA nucleic acid molecule encoding a canine IL-5 protein was isolated by PCR amplification from a canine PBMC cDNA library. The library was a *C. familiaris* mitogen activated PBMC cDNA library that was constructed in the Uni-ZAP® XR vector (available from Stratagene Cloning Systems, La Jolla, Calif.), using Stratagene's ZAP-cDNA® Synthesis Kit and the manufacturer's protocol. The mRNA was isolated from *C. familiaris* peripheral blood mononuclear cells about 18 hours after they were activated by a polyclonal activating agent in culture.

The PCR products were cloned and sequenced using Amplitaq DNA polymerase (available from PE Applied Biosystems Inc, Foster City, Calif.) under the following PCR protocol: one initial denaturation step at 95° C. for 3 minutes; then 46 cycles of the following: 94° C. for 45 seconds, then 48° C. for 45 seconds, then 72° C. for 1 minute 45 seconds; followed by a final extension at 72° C. for 8 minutes. Degenerate oligonucleotide primers were designed in accordance with conserved regions of human and cat IL-5 gene sequences available in GenBank: sense primer, 5' ATGCACTTTC TTTGCC 3', denoted herein as SEQ ID NO:1; antisense primer 1, 5' CTGGAGGAAA AKACTTCRAT GATTCT-GATA TCTGAAATAT AT 3', denoted herein as SEQ ID NO:2; and antisense primer 2, 5' CTGACYCTTK STTGGSCCTC ATTCTCA 3', denoted herein as SEQ ID NO:3, where K was G or T, R was either A or G, S was either G or C, and Y was either T or C.

An about 610-nucleotide canine IL-5 nucleic acid molecule, denoted nCaIL-$5_{610}$, was obtained using primers having SEQ ID NO:1 and SEQ ID NO:2, respectively. The sequence of the coding strand of nCaIL-$5_{610}$, is represented herein as SEQ ID NO:4. The reverse complement of SEQ ID NO:4 is referred to herein as SEQ ID NO:6. Translation of SEQ ID NO:4 suggests that nucleic acid molecule nCaIL-$5_{610}$ encodes an IL-5 protein of 134 amino acids, denoted herein as PCaIL-$5_{134}$, the amino acid sequence of which is presented in SEQ ID NO:5, assuming an open reading frame having an initiation codon spanning from nucleotide 29 through nucleotide 31 of SEQ ID NO:4 and a stop codon spanning from nucleotide 431 through nucleotide 433 of SEQ ID NO:4. The coding region encoding PCaIL-$5_{134}$, not including the termination codon, is presented herein as nCaIL-$5_{402}$, which has the nucleotide sequence SEQ ID NO:7 (the coding strand) and SEQ ID NO:8 (the complementary strand).

An about 488-nucleotide fragment, denoted herein as nCaIL-$5_{488}$, isolated by PCR with primers having SEQ ID NO:1 and SEQ ID NO:2, respectively, corresponds to nucleotide 1 through nucleotide 488 of nCaIL-$5_{610}$.

A putative signal sequence coding region extends from nucleotide 29 through nucleotide 85 of SEQ ID NO:4. The proposed mature protein, denoted herein as PCaIL-$5_{115}$, represented by SEQ ID NO:10, contains about 115 amino acids, extending from residue 20 though residue 134 of SEQ ID NO:5. The nucleotide sequence encoding PCaIL-$5_{115}$, which extends from nucleotide 86 through nucleotide 430 of SEQ ID NO:4, is denoted herein as nucleic acid molecule nCaIL-$5_{345}$, represented by SEQ ID NO:9 (coding strand) and SEQ ID NO:11 (the complement strand).

Sequence analysis was performed with DNAsis™ using the alignment settings of: gap penalty set at 5; number of top diagonals set at 5; fixed gap penalty set at 10; k-tuple set at 2; window size set at 5 and floating gap penalty set at 10. At the amino acid level, PCaIL-$5_{134}$ shared 82.8% and 57.4% identity with feline and human IL-5 proteins, respectively (Padrid et al., *Am. J. Vet. Res., vol.* 59, pp. 1263-1269, 1998; Azuma et al., *Nucleic Acids Res., vol.* 14, pp. 9149-9158, 1986). At the nucleotide level, nCaIL-$5_{610}$ shared 81.7% and 75% identity with the cDNA sequences of the feline and human IL-5, respectively.

B. Expression of Canine IL-5 in *Pichia*

This example describes the expression in *Pichia* of a canine IL-5 cDNA fragment, namely a canine IL-5 nucleic acid molecule denoted nCaIL-$5_{348}$, the coding strand of which consists of nucleotides 86-433 of SEQ ID NO:4, and as such, encodes a predicted mature canine IL-5 protein having SEQ ID NO:10. Nucleic acid molecule nCaIL-$5_{348}$, was PCR amplified from nCaIL-5$_{610}$ using sense primer 5' GGGCTC-GAGA AAAGATTTGC TGTAGAAAAT CCCATG 3' denoted herein as SEQ ID NO:12, with nucleotides 16-36 corresponding to nucleotides 86-106 of SEQ ID NO:4; and antisense primer 5'CCCGCGGCCG CTCAACTTTC CGGT-GTCCAC TC 3', denoted herein as SEQ ID NO:13, with nucleotides 12-32 corresponding to the reverse complement of nucleotides 413-433 of SEQ ID NO:4. To facilitate cloning, an XhoI site (shown in bold) was added to the sense primer and a NotI site (shown in bold) was added to the antisense primer. The PCR-amplified fragment was digested with restriction endonucleases XhoI and NotI, gel purified and ligated into pPICZαA plasmid vector, available from Invitrogen, that had been digested by Xho I and Not I and gel purified, to produce recombinant molecule pPICZαA-nCaIL-5$_{348}$. The insert in the recombinant molecule was verified by DNA sequencing The recombinant molecule was used to transform *Pichia pastoris* strain X-33 by electroporation to produce recombinant cell *Pichia*-pPICZαA-nCaIL-5$_{348}$. Recombinant cell *Pichia*-pPICZαA-nCaIL-5$_{348}$, was cultured using techniques known to those skilled in the art and IL-5 expression was induced with methanol. The supernatant was recovered and submitted to SDS-PAGE. Silver staining of the resultant gel indicated a band of about 18 kDa only seen in the supernatant of *Pichia* transformed with recombinant molecule pPICZαA-nCaIL-5$_{348}$.

Example 2

This example describes the isolation and characterization of the canine IL-5 gene, its expression, and biological activity of the recombinantly produced protein.

A. Cloning of Canine IL-5 Genomic DNA

In order to characterize the structure of the canine IL-5 gene, a DNA fragment was isolated from dog genomic DNA (Clontech, Palo Alto, Calif.) by PCR using primers DF8, 5' AGGCAAACACTGAACATTTC3', denoted herein as SEQ ID NO:14, and DB8, 5'TCTCCAAAATCTTCCACTAC3', denoted herein as SEQ ID NO:15, and the methods described in Example 1. The PCR product was isolated, subcloned into the pCR2.1 plasmid using TA cloning kit (Invitrogen, Carlsbad, Calif.), and sequenced. Automated cycle sequencing of DNA samples was performed using an ABI PRISM™ Model 377 and reaction kit from PE Applied Biosystems (Foster City, Calif.). Sequence analysis was performed with DNASIS (Hitachi, San Bruno, Calif.) using default alignment settings.

A 1658-bp fragment, nCaIL-5$_{1658}$, was isolated from canine genomic DNA and sequenced. The coding strand of the genomic sequence is designated herein as SEQ ID NO:18. The noncoding strand is designated herein as SEQ ID NO:19. Alignment of genomic DNA reveals three introns of 203 bp, 869 bp, and 118 bp, respectively, in the coding region of canine IL-5. This gene structure is similar to that of the previously characterized human and mouse IL-5 genes (Campbell, H. D., et al., (1987) Proc. Natl. Acad. Sci., USA 84:6629-6633; Tanabe, T., et al (1987)., J. Biol. Chem. 262: 16580-16584; Campbell, H. D., et al, (1988), Eur. J. Biochem). Furthermore, the three introns are located at the same relative sites, and the sequences surrounding the exon-intron junctions are similar among IL-S genes of the dog, human and mouse. Such conservation also suggests that the expression of canine IL-5 genes is likely subject to regulation similar to the well-studied expression of mouse and human IL-5 genes. (Karlen, S., et al, (1998), Int. Rev. Immunol. 16:227-247).

B. Detection of Canine IL-5 mRNA Expression by RT-PCR

Coupled reverse transcriptase-polymerase chain reaction (RT-PCR) was carried out to detect the expression of canine IL-5 transcripts in cells from lymph nodes and peripheral blood. Isolation of total RNA from lymph node cells and synthesis of first strand cDNA were performed as described above using the canine IL-5-specific primers DF8 and DB8. As a control, PCR was also performed on the "house-keeping" gene HPRT using primers 3F, 5'TCAAGGGAGGC-TATAAATTC3', denoted herein as SEQ ID NO:16, and 8R, 5'TTATAGTCAAGGGCATATCC3', denoted herein as SEQ ID NO:17. Amplification of cDNA samples diluted at 1:10 (for IL-5) or 1:50 (for HPRT) and genomic DNA (Clontech) was performed in a 30 µl reaction. PCR conditions were as follows: One initial denaturation step at 95° C. for 3 min; then 38 cycles (for IL-5) or 35 cycles (for HPRT) at 94° C. for 45 sec, 60° C. (for IL-5) or 63° C. (for HPRT) for 45 sec, and 72° C. for 1 min and 45 sec; and a final extension at 72° C. for 8 min. Half of the PCR product was analyzed by agarose gel electrophoresis in the presence of ethidium bromide. Pfu DNA polymerase (2.5 U/100 µl reaction)(Stratagene, La Jolla, Calif.) was used in the RT-PCR.

A 468-bp band was predominantly amplified by RT-PCR using primers DF8 and DB8. Sometimes a larger band of approximately 671-bp was also seen, using the same primers. DNA sequencing indicated that this larger band was derived from transcripts that contained unspliced intron 1. This incompletely spliced transcript is designated SEQ ID NO: 21. When genomic DNA was used in the PCR, the 1658-bp band characterized above was amplified.

C. TF-1 Cell Proliferation Assay

The protein produced according to Example 1 B was assayed for biological activity. The N-terminal amino acid sequence (FAVENPMNRLVAETL) (SEQ ID NO:20) confirmed the identity of this protein as recombinant dog IL-5. The predicted molecular weight of mature canine IL-5 polypeptide is 13 kDa, suggesting that the recombinant canine IL-5 is glycosylated in *P. pastoris*.

A human erythroleukaemia cell line, TF-1 (Kitamura, T., et al, (1989). J. Cell. Physiol. 140:323-334), (R&D Systems, Minneapolis, Minn.), was maintained in RPMI-1640 media supplemented with 2 mM L-glutamine, 5 µg/ml gentamicin, 5% FBS and 2 ng/ml recombinant human GM-CSF (rhuGM-CSF, R&D Systems) called Tissue Culture Media-TF-1 (TCM-TF-1). Cells were grown in 5% $CO_2$ at 37° C.

Prior to cell proliferation assays, TF-1 cells were washed extensively to remove rhuGM-CSF, and then plated at $1\times10^4$ cells per well in 96-well flat bottom plates. Supernatants from either *P. pastoris* X-33 or the recombinant *P. pastoris* containing the canine IL-5 gene were dialyzed overnight (using 10,000 MW cut-off membranes) at 4° C. against phosphate buffered saline, diluted to the appropriate concentration in TCM-TF-1 without rhuGM-CSF, and filter sterilized. Cells and supernatants were incubated for 48 hours in 5% $CO_2$ at 37° C., pulsed with 1 µCi/well tritiated thymidine (ICN Pharmaceuticals, Irvine, Calif.), and incubated for an additional 18 hours. Contents of the wells were harvested onto glass fiber filters and counted in a Wallac Trilux 1450 scintillation counter (Wallac Inc., Gaithersburg, Md.).

The TF-1 cells respond in a dose-dependent fashion to the *P. pastoris* expressed canine IL-5. In contrast, supernatants from the induced *P. pastoris* X-33, transformed with the empty vector, failed to stimulate TF-1 cell proliferation. The bioassay is extremely sensitive; based on experiments with recombinant human IL-5, as little as 150 pg/ml can stimulate TF-1 proliferation. Using human IL-5 as the standard, and assuming that the IL-5 works equivalently across species, it is estimated that the *P. pastoris* IL-5 supernatants contain around 20 ng/ml canine IL-5.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein comprising the amino acid sequence set forth in SEQ ID NO:5 or SEQ ID NO; 10.

2. An isolated protein encoded by a nucleic acid molecule comprising the nucleotide sequence set forth in SEQ ID NO:4, SEQ ID NO:7 or SEQ ID NO:9.

3. An isolated protein consisting of the amino acid sequence set forth in SEQ ID NO:5 or SEQ ID NO: 10.

* * * * *